US012569316B2

(12) United States Patent
Feng et al.

(10) Patent No.: US 12,569,316 B2
(45) Date of Patent: Mar. 10, 2026

(54) ENDOSCOPIC SURGERY PLATFORM

(71) Applicants: Jilin University, Changchun (CN);
Jilin Jinbohong Intelligent Technology Co., Ltd., Changchun (CN)

(72) Inventors: Mei Feng, Changchun (CN); Yanlei Gong, Changchun (CN); Yongkang Li, Changchun (CN); Xiuquan Lu, Changchun (CN); Kewen Song, Changchun (CN); Chao Wang, Changchun (CN); Jinhui Li, Changchun (CN); Jiaqi Ren, Changchun (CN); Hengyue Su, Changchun (CN); Shijie Liu, Changchun (CN)

(73) Assignees: Jilin University, Changchun (CN);
Jilin Jinbohong Intelligent Technology Co., LTD., Changchun (CN)

( * ) Notice: Subject to any disclaimer, the term of this patent is extended or adjusted under 35 U.S.C. 154(b) by 285 days.

(21) Appl. No.: 18/374,674

(22) Filed: Sep. 29, 2023

(65) Prior Publication Data

US 2024/0358473 A1    Oct. 31, 2024

(30) Foreign Application Priority Data

Apr. 27, 2023    (CN) .......................... 202310476080.7

(51) Int. Cl.
*A61B 90/50* (2016.01)
*A61B 1/00* (2006.01)
*A61G 13/06* (2006.01)
*A61G 13/10* (2006.01)

(52) U.S. Cl.
CPC .......... *A61B 90/50* (2016.02); *A61B 1/00149* (2013.01); *A61G 13/06* (2013.01); *A61G 13/101* (2013.01)

(58) Field of Classification Search
CPC .... A61B 1/00149; A61B 90/50; A61G 13/06; A61G 13/101
See application file for complete search history.

(56) References Cited

U.S. PATENT DOCUMENTS

2016/0331613 A1* 11/2016 Lee ........................ A61G 7/005

* cited by examiner

*Primary Examiner* — Scott Luan
(74) *Attorney, Agent, or Firm* — Addison D. Ault; IPGentleman Intellectual Property Services, LLC

(57) ABSTRACT

An endoscopic surgery platform includes a surgical bed and multiple surgical manipulators. Multiple surgical manipulators are arranged in a matrix on both sides of the surgical bed, and a positioning mechanism is arranged at the bottom of the surgical bed. The surgical manipulator can be stored at the bottom of the surgical bed through the positioning mechanism. The positioning mechanism includes a plurality of surgical manipulators positioned on the bottom of the surgical bed, a plurality of lateral moving pairs for moving along the length direction of the surgical bed, and multiple longitudinal moving pairs connected to the output end of multiple lateral moving pairs respectively and used to move along the width direction of the surgical bed. Longitudinal moving pair, lateral moving pairs and surgical manipulators are connected one by one.

9 Claims, 10 Drawing Sheets

Parallelogram mechanism type

Spherical mechanism type

Triangular mechanism type

Symmetric rod configuration 251
252
253
254
255
256

ENDOSCOPIC SURGERY PLATFORM

CROSS REFERENCE TO THE RELATED APPLICATIONS

This application is based upon and claims priority to Chinese Patent Application No. 202310476080.7, filed on Apr. 27, 2023, the entire contents of which are incorporated herein by reference.

TECHNICAL FIELD

The present invention relates to the technical field of medical equipment for thoracic and abdominal endoscopic surgery and particularly relates to an endoscopic surgery platform.

BACKGROUND

Minimally invasive surgery has many advantages over traditional open surgery, including reducing pain, shortening hospital stays, faster recovery and less trauma. The advantages of fewer complications and less fatigue for doctors are widely used.

In order to decrease the exhaustion of medical personnel and enhance surgical accuracy, current technology has produced a combination of robotics and minimal invasive surgery. The existing robots that assist minimally invasive surgery have the following defects:

1. In terms of the combination of manipulators, since the thoracic/laparoscopic surgical robot needs to hold a variety of surgical instruments and endoscopes for surgery, a general surgical robot is designed with four manipulators, of which three are used to hold surgical instruments such as surgical grasping forceps, surgical scissors, needle-holding forceps, etc. To complete surgical operations such as traction, stripping tissue, and needle stitching, and the remaining manipulator is used to hold the endoscope and provide visual guidance to the lesion area during the operation. At present, according to the different combination forms of multiple manipulators, the manipulators of minimally invasive surgical robots are mainly divided into integrated and split types. Wherein, multiple manipulators of the integrated manipulator are fixed on a base, and the representative product of the integrated manipulator is the Da Vinci surgical robot of the United States. The manipulator of the robot has a compact structure and occupies a small space, and the relative position between the manipulators is determined, but interference between the manipulators is easy to occur, which increases the difficulty of preoperative positioning. The split type is that each manipulator is installed on different bases, and each manipulator is independent of others. The manipulators of minimally invasive surgical robots such as Senhance in Canada and Huaque-II in China adopt a split structure. The manipulators of the split surgical robot are independent of others, and the preoperative positioning is flexible. It is easy to choose the appropriate insertion position and angle of the surgical instrument, but it takes up a large space in the operating room and is difficult to determine the relative position between the manipulators.

In summary, based on the combination of the above-mentioned manipulators, the current endoscopic surgical robot has a single application scenario and a solidified operation mode, which is only applicable to the master-slave operation mode (that is, a doctor sits in front of the control table to operate the main hand of the surgical robot to control the surgical instruments held by the manipulator and performs the operation mode. For example, a doctor sits in front of the main console of the Da Vinci robot system for surgical operation), which can not meet the doctor's needs for human-machine collaborative operation and surgical operation habits, and it is necessary to set up surgical incisions and adjust multiple manipulators time lengths before surgery, which does not meet the requirements of specialized surgery.

2. Telecentric mechanism: as shown in FIG. 1, in minimally invasive surgery, to prevent surgical instruments and endoscopes from scratching or pulling the body surface incision during surgery, surgical instruments and endoscopes are required to make a "fixed point" motion around the body surface incision (that is, two swings around the tangential direction of the body surface incision, translation along the axis of the surgical instrument itself, and rotation around the axis of the surgical instrument itself), and the mechanism that realizes the 'fixed-point' motion is called a telecentric mechanism, where the "fixed-point" is generally called telecentric point. In the minimally invasive surgical robot system, the telecentric mechanism is located at the end of the manipulator and is used to clamp surgical instruments or endoscopes, and the stiffness, accuracy, stability and flexibility of the telecentric mechanism directly affect the performance of surgical instruments and endoscopes during surgery. Therefore, the telecentric mechanism is one of the key technologies for the design and development of minimally invasive surgical robots.

At present, the telecentric mechanism adopts the parallelogram mechanism, the spherical mechanism, the triangular mechanism, the parallel mechanism and the arc orbit mechanism to realize "fixed-point" motion. Wherein, as shown in FIG. 2, although the number of joints of the parallelogram mechanism is low, due to its multi-segment steel strip, the stiffness of the mechanism is low, and special equipment is needed for assembly, and the cost of subsequent assembly and maintenance is high; as shown in FIG. 3, the number of joints and links of the spherical mechanism is low, and the structure is compact, but the stiffness and stability are poor; as shown in FIG. 4, the triangular mechanism has a simple structure and high stiffness, but the joint coupling is obvious and prone to interference problems: as shown in FIG. 5, the parallel mechanism has high stiffness and compact structure, but it has the disadvantages of strong motion coupling, high machining accuracy and small working space, which makes it difficult to solve the forward and inverse kinematics of the robot system; There are only two joints in the circular arc track mechanism, and the structure is simple. The disadvantage is that the volume is large and the drive design is difficult.

In summary, most of the existing telecentric mechanisms have problems such as large volume, easy collision and interference between the manipulators, and small effective motion space, and when they are not used, they are difficult to be bundled under the surgical table, occupying a large space and affecting the separate use of the surgical table.

SUMMARY

To solve the above problems, the present invention provides an endoscopic surgery platform, which is different from the existing fully master-slave mode of abdominal minimally invasive surgery robot, and it can set different number of manipulators according to different surgical scene requirements: a single manipulator is used as a endoscope holding robot, 2-3 manipulators are used as assistant robots, and 4 manipulators are used as fully master-slave mode surgical robots.

To achieve the above purpose, the present invention provides an endoscopic surgery platform, comprising a surgical bed and surgical manipulators, wherein the surgical manipulators are arranged on both sides of the surgical bed in a matrix arrangement. A positioning mechanism is arranged at a bottom of the surgical bed, and the surgical manipulators are stored at the bottom of the operating bed by the positioning mechanism.

the positioning mechanism comprises: the surgical manipulators positioned on the bottom of the surgical bed, lateral moving pairs for moving along a length direction of the surgical bed, and longitudinal moving pairs connected to an output end of the lateral moving pairs respectively and used to move along a width direction of the surgical bed, wherein the longitudinal moving pairs, the lateral moving pairs and the surgical manipulators are connected one by one.

Preferably, the surgical bed includes a surgical table, a support frame, a base and a moving caster arranged from top to bottom, each of the lateral moving pairs comprises a lateral sliding rail fixed at the bottom of the surgical table, a positioning iron bar arranged in parallel with the lateral sliding rail, and a lateral moving platform, one side of the lateral moving platform is slidingly connected to the lateral sliding rail through a slider, and the side of the lateral moving platform facing the lateral sliding rail is also connected to the positioning iron bar by an electromagnet Preferably, the longitudinal moving pair includes a longitudinal slide fixed on the other side of the lateral moving platform, a longitudinal moving platform slidingly connected to the longitudinal slide on one side through a slider, and a guide rail clamp for positioning the longitudinal moving platform to the longitudinal slide, the other side of the longitudinal moving platform is connected to the surgical manipulator.

Preferably, the bottom of the surgical table and the position parallel to the lateral slide rail are also fixed with a long magnetic grating ruler; the bottom of the lateral moving platform and the position parallel to the longitudinal slide rail are also fixed with a short magnetic grating ruler.

On the lateral and longitudinal moving platforms, reading heads suitable for long magnetic grating ruler and short magnetic grating ruler are set respectively.

Preferably, the surgical manipulator includes a rotary storage mechanism, a lifting mechanism and a telecentric mechanism connected to a longitudinal moving platform in turn; The telecentric mechanism is a composite structure composed of an axial rotation unit, a deflection unit and a translational probe unit.

Preferably, the rotary storage mechanism includes a storage joint module connected by a vertical mounting column and a longitudinal moving platform; The output end of the storage joint module is connected to one end of the horizontal connecting column.

Preferably, the lifting mechanism includes a lifting column connected to the other end of the T-shaped connecting column and the horizontal connecting column, a lifting shell connected to the vertical sliding of the lifting column, and a driving component for driving the lifting shell to slide along the lifting column;

the driving component includes a worm gear motor fixed in the lifting shell by the lifting connecting plate, a transmission gear connected to the output end of the worm gear motor and a vertical rack meshing with the transmission gear; the vertical rack is fixed on the inner wall of the lifting column;

the inner wall of the lifting column is also fixed with a vertical guide slide rail, which is fixed on the lifting connection plate and the position corresponding to the vertical guide slide rail; The vertical guide slider is slidingly connected to the vertical guide slide rail Preferably, the axial rotation unit of the telecentric mechanism includes an axial rotation joint module fixedly connected to the lifting shell; the output end of the axial rotation joint module is connected to the deflection unit through the lateral rotation shaft.

Preferably, the deflection unit of the telecentric mechanism includes an arc installation plate, an arc slide rail fixed on one side of the arc installation plate, multiple guide wheels rotating on the other side of the arc installation plate, and the drive wheel and the driven wheel, and multiple guide wheels, drive wheels and driven wheels are enclosed in an arc shape with the same radian as the arc slide rail;

the drive wheels are concentrically connected to the first transmission bevel gear, the first transmission bevel gear is engaged with the second transmission bevel gear, and the second transmission bevel gear is connected to the output shaft of the deflection motor fixed on the lateral shaft;

the drive wheel, multiple guiding wheels and driven wheels are connected by wire rope transmission, and the wire rope is connected to the translational penetration unit through the arc hole opened on the arc installation plate, and the translational penetration unit is also connected to the arc slide Preferably, the translational penetration unit of the telecentric mechanism includes a translational probe motor, a screw and a ball nut connected in turn, and the ball nut is connected to the surgical instrument mounting plate, and the surgical instrument is installed on the surgical instrument mounting plate;

both sides of the surgical instrument mounting plate are connected by sliding block and linear slide rail, and the linear slide rails on both sides are fixedly connected to both sides of the inner side of the protective cover, the middle of the protective cover is connected to the rotation of both ends of the screw rod, the outer side of the protective cover is connected by sliding block and arc slide rail, the outer side of the protective cover is also connected by wedge block and arc mounting plate, the wedge block is fixedly connected to one end of the double head screw, the other end of the double head screw is fixedly connected to the wire rope after passing through the arc hole.

The present invention has the following beneficial effects:

1. to address the traditional integrated manipulator's shortcomings of interfering with each other, large space occupation, and difficulty in determining the relative position between multiple manipulators, the present invention introduces an endoscopic surgery platform. This platform combines the surgical manipulator and the operating bed, which are arranged in pairs on the left and right sides of the operating table. Each manipulator can operate independently, and its preoperative position is flexible and doesn't interfere with other manipulators' movement.

2. multiple manipulators are mounted on slide rails at the bottom of the operating bed. This allows for fixed relative positioning and efficient storage under the operating bed, freeing up valuable space and making them well-suited for small to medium-sized operating rooms.

3. multiple manipulators are constructed uniformly and can hold various surgical tools, including surgical instruments and endoscopes, all of which have excellent interchangeability. The number of manipulators utilized can be adjusted according to the specific surgical requirements: for instance, a single manipulator may be employed as an endoscope holding robot, while 2-3 manipulators may act as assistant robots, and four manipulators can be used to operate surgical robots in full master-slave mode.

The multi-arm structure of the endoscopic surgery platform offers several advantages. Firstly, it allows for man-machine collaborative operation, enabling surgeons to work alongside surgical robots at the surgery site. This approach combines the extensive experience gained by doctors in traditional minimally invasive surgery with the advantages provided by machines for conventional surgical operations. Secondly, the new multi-scene man-machine collaborative operation mode significantly reduces the preoperative incision preparation time and the time needed to adjust the manipulator posture, compared to the current master-slave operation mode used in robot-assisted minimally invasive surgery. This is more conducive to reducing the total operation time and improving the overall outcome of the surgery. Thirdly, this multi-scene human-machine collaboration operation mode is more suitable for specialized surgery practices, allowing doctors to configure the robot human-machine collaboration mode to meet the requirements of individualized specialized surgeries.

4. Currently, most telecentric mechanisms used in thoracic/laparoscopic surgical robots suffer from drawbacks such as large volume, potential collision and interference between manipulators, and limited effective motion space. To overcome these challenges, this study proposes a novel telecentric mechanism that utilizes an axial rotary joint to enable tangential body surface incision movements, and an arc slide rail to guide these movements. The mechanism employs a modular design scheme for the driving and transmission layers, which effectively resolves the issue of difficult driving design for circular orbit telecentric mechanisms. Additionally, the planar structure of the telecentric mechanism addresses the collision and interference issues between manipulators, improves the motion space of the manipulator, and results in a more compact structure with reduced volume and weight.

The technical scheme of the invention is elaborated in detail below, with reference to the accompanying drawings and embodiments.

Figure 1:
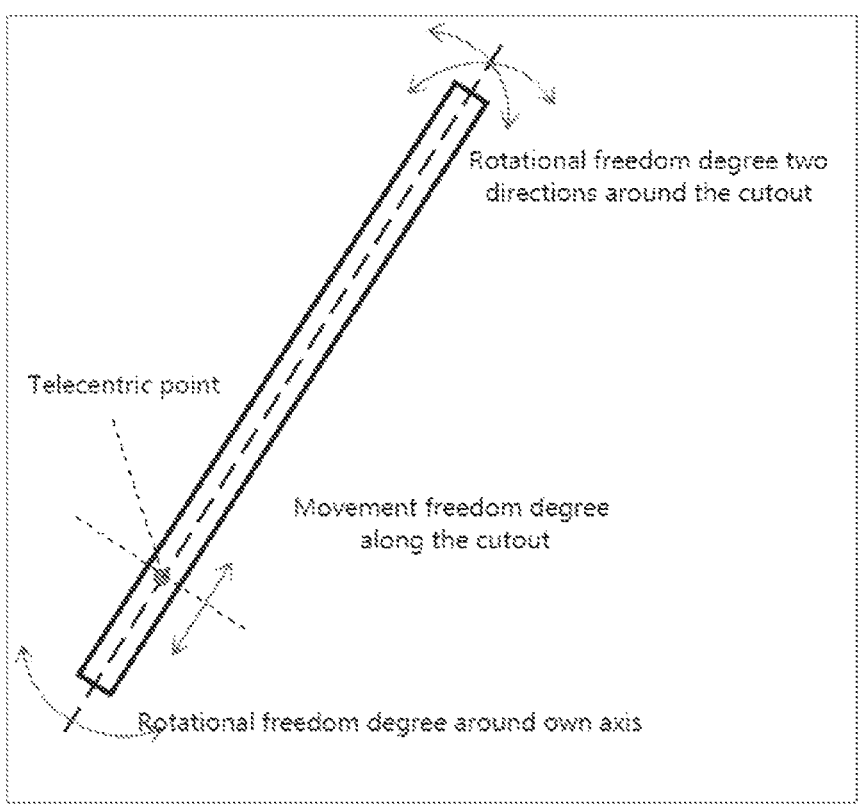
FIG. 1 is the action diagram of the existing telecentric mechanism.
Figure 2:
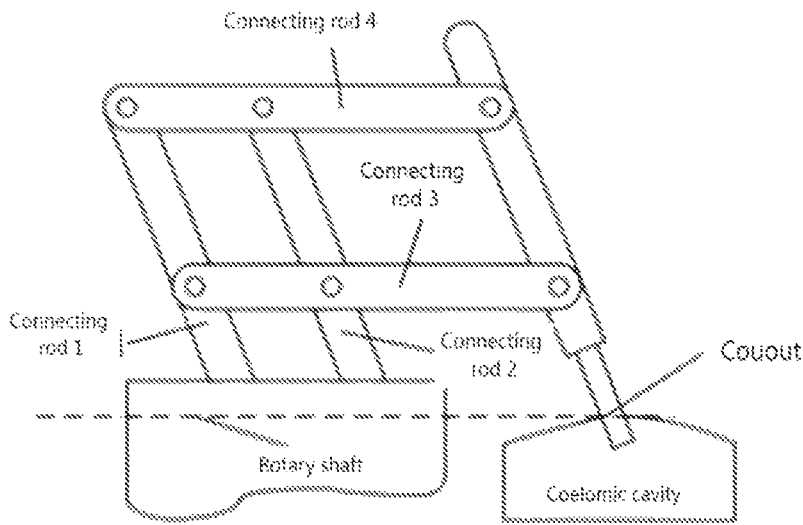
FIG. 2 is the schematic diagram of the existing parallelogram mechanism.
Figure 3:
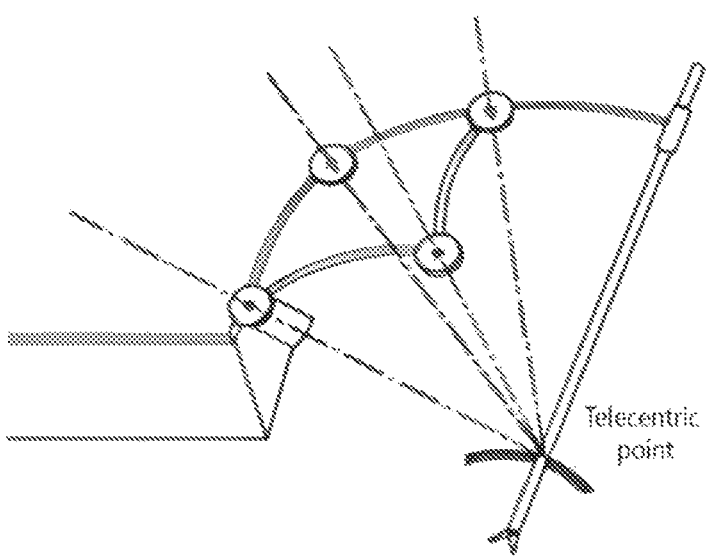
FIG. 3 is the schematic diagram of the existing spherical mechanism structure.
Figure 4:
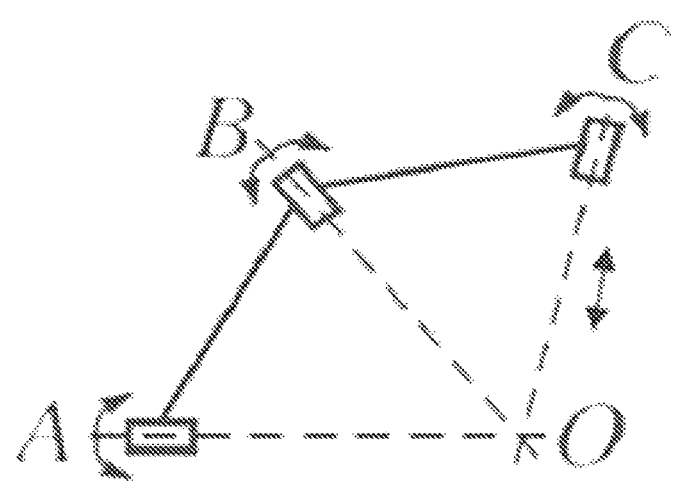
FIG. 4 is the schematic diagram of the existing triangular mechanism structure.
Figure 5:
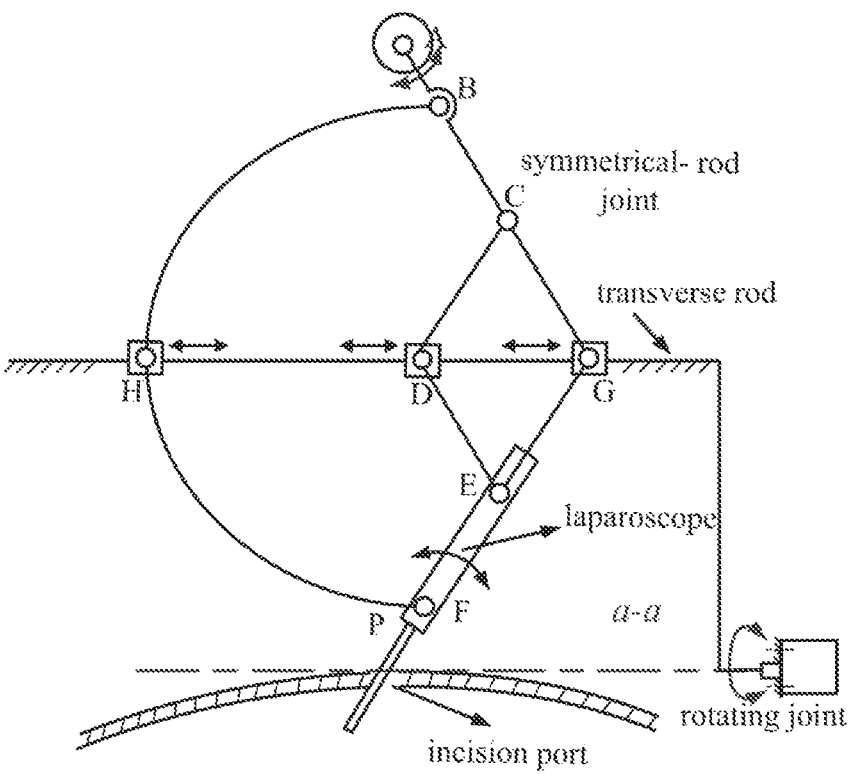
FIG. 5 is the structure diagram of the existing parallel mechanism.
Figure 6:
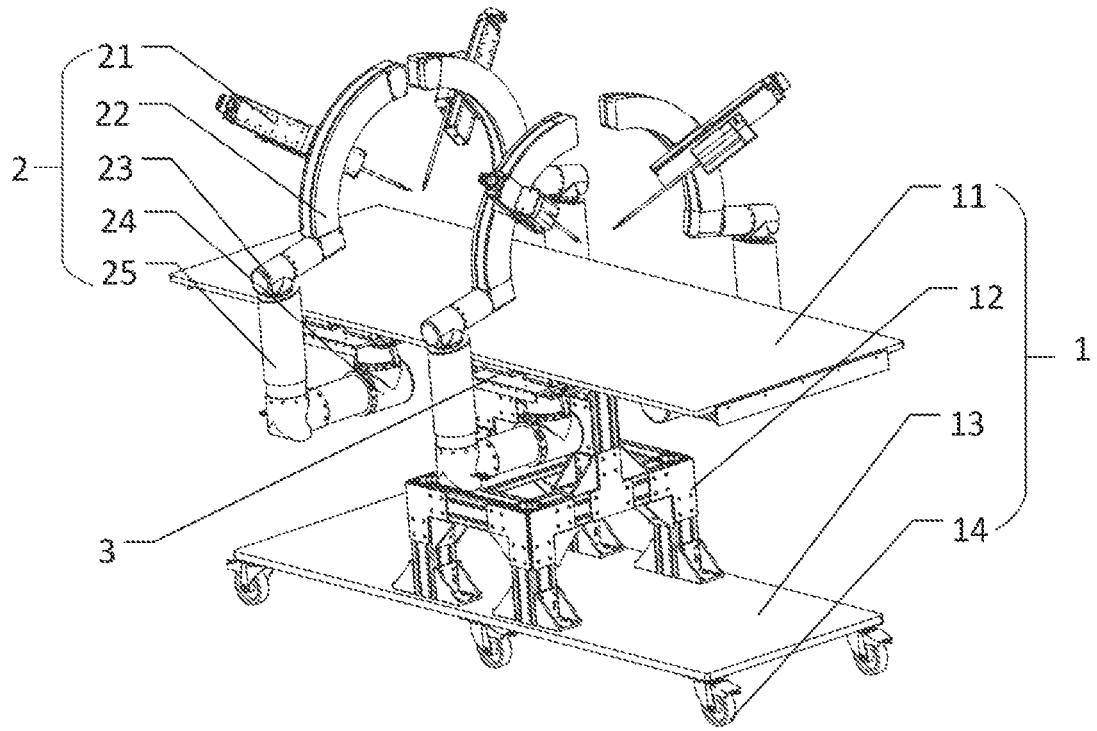
FIG. 6 shows the overall structure diagram of an endoscopic surgery platform of the present invention.
Figure 7:
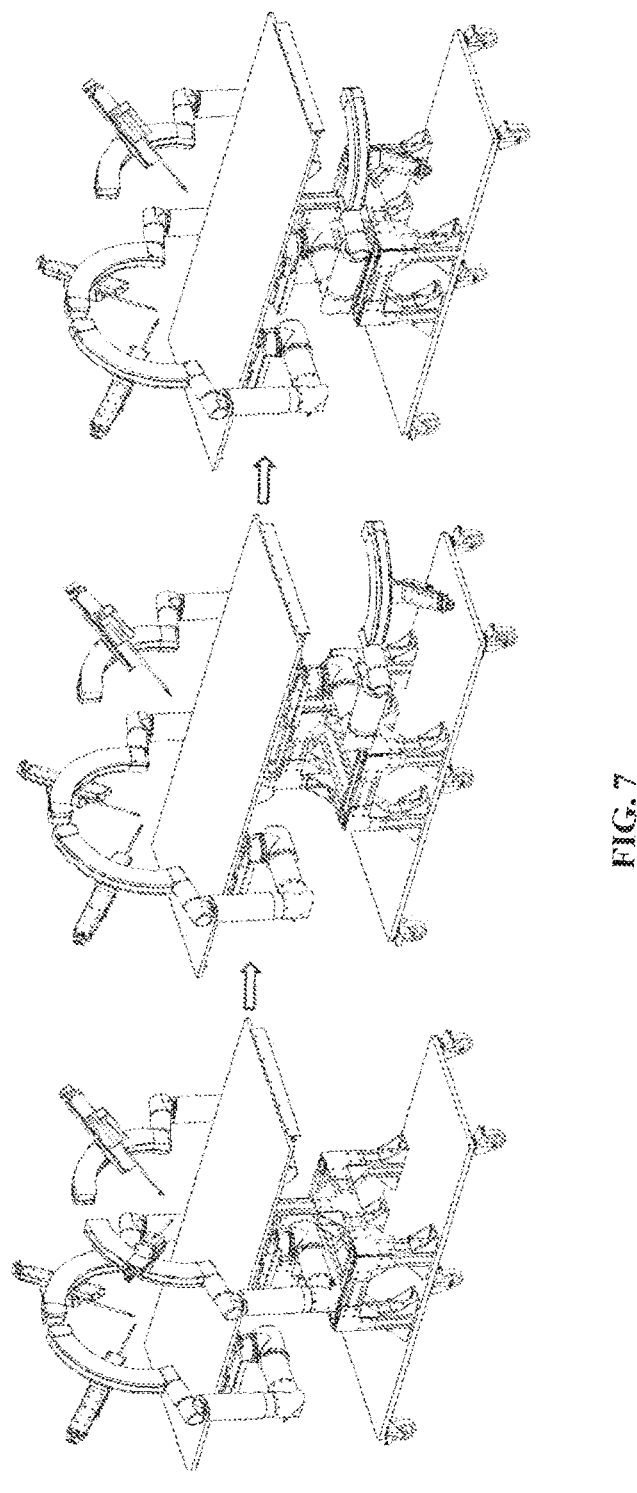
FIG. 7 is a schematic diagram of the storage process of an endoscopic surgery platform of the present invention.
Figure 8:
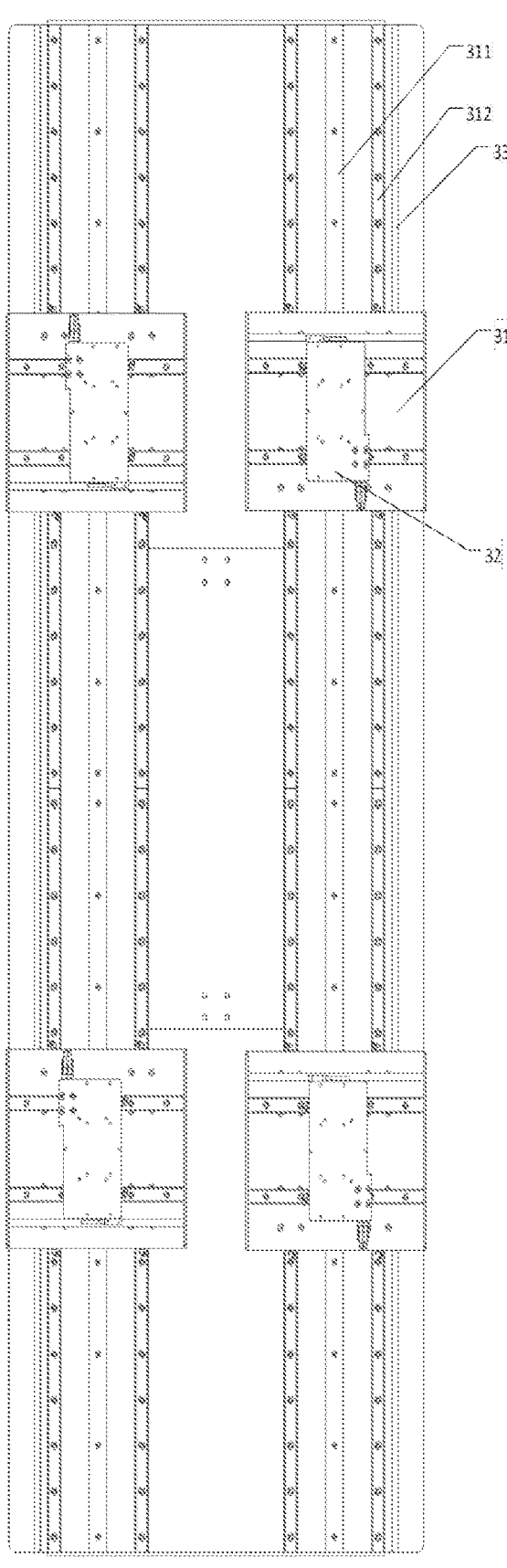
FIG. 8 is a schematic diagram of the positioning mechanism structure of an endoscopic surgery platform of the present invention.
Figure 9:
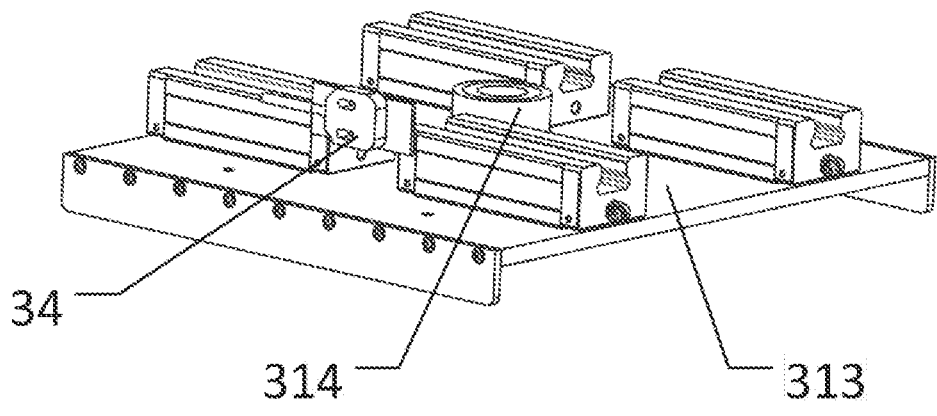
FIG. 9 is a schematic diagram of the lateral moving platform structure of an endoscopic surgery platform of the present invention.
Figure 10:
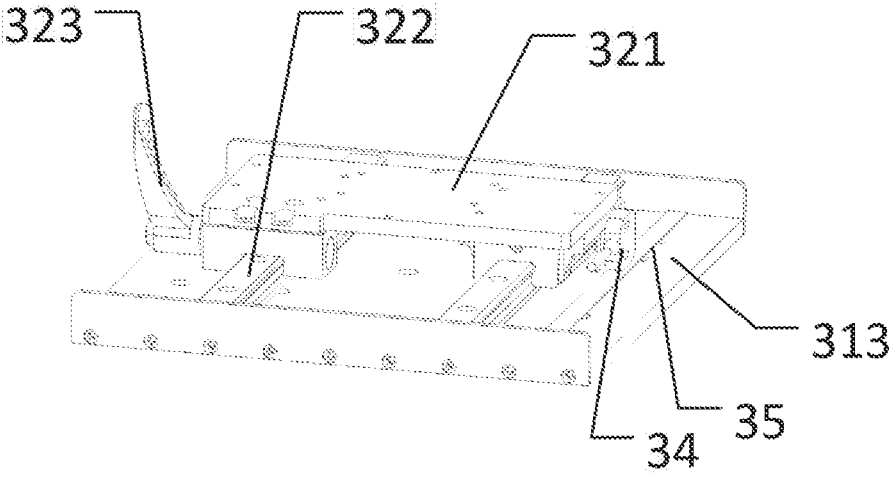
FIG. 10 is a schematic diagram of the longitudinal moving platform structure of an endoscopic surgery platform of the present invention.
Figure 11:
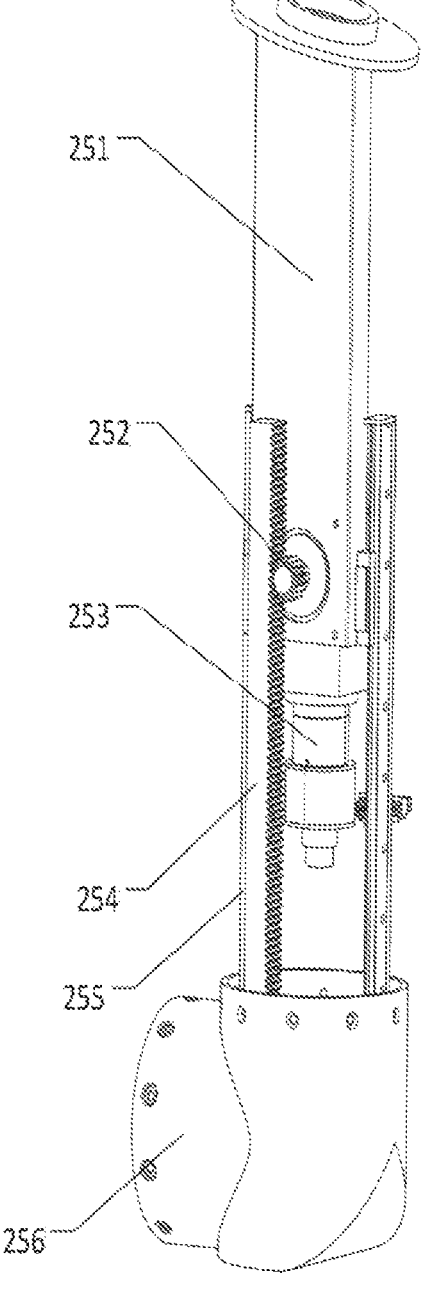
FIG. 11 is the schematic diagram of the lifting mechanism of the novel endoscopic surgery platform of the present invention.
Figure 12:
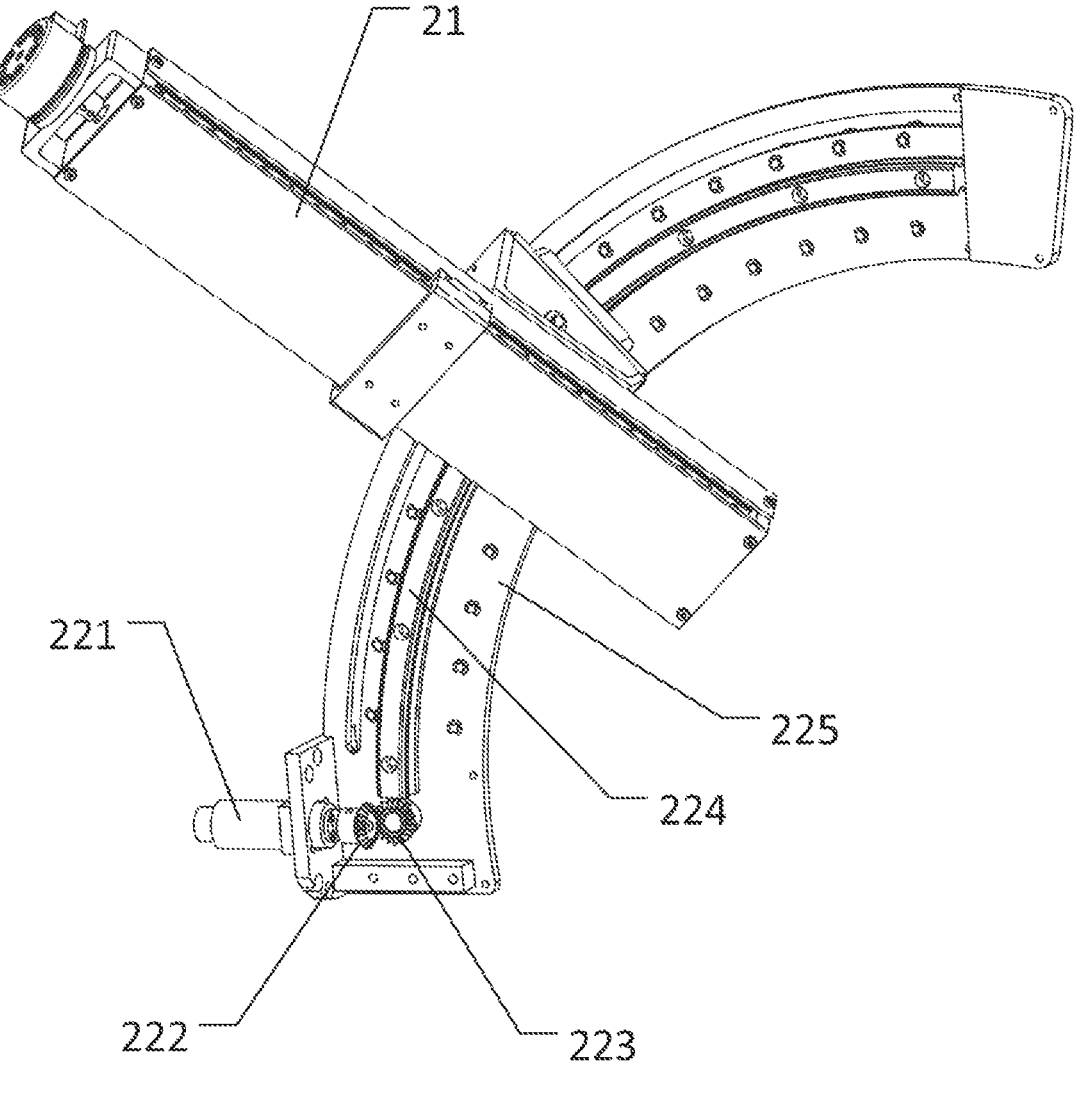
FIG. 12 is the internal diagram of the deflection unit of an endoscopic surgery platform of the present invention.
Figure 13:
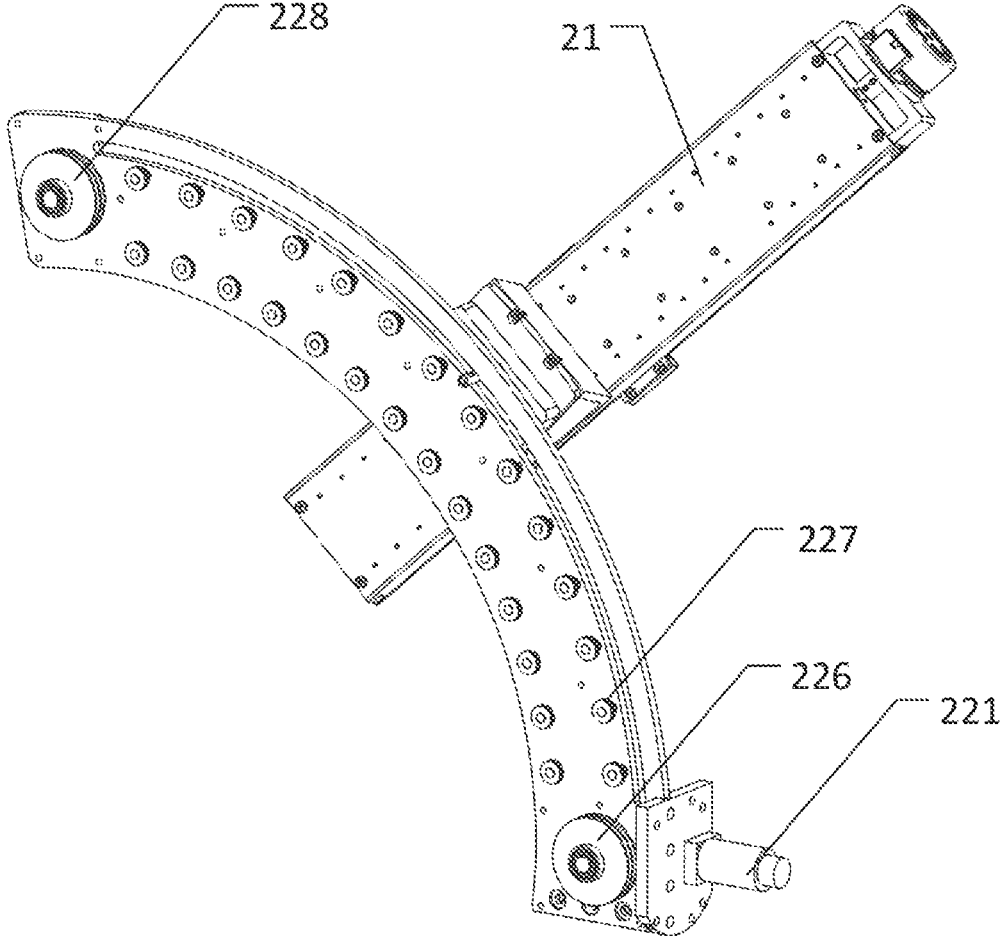
FIG. 13 is the back view of the deflection unit of a novel endoscopic surgical platform of the present invention.
Figure 14:
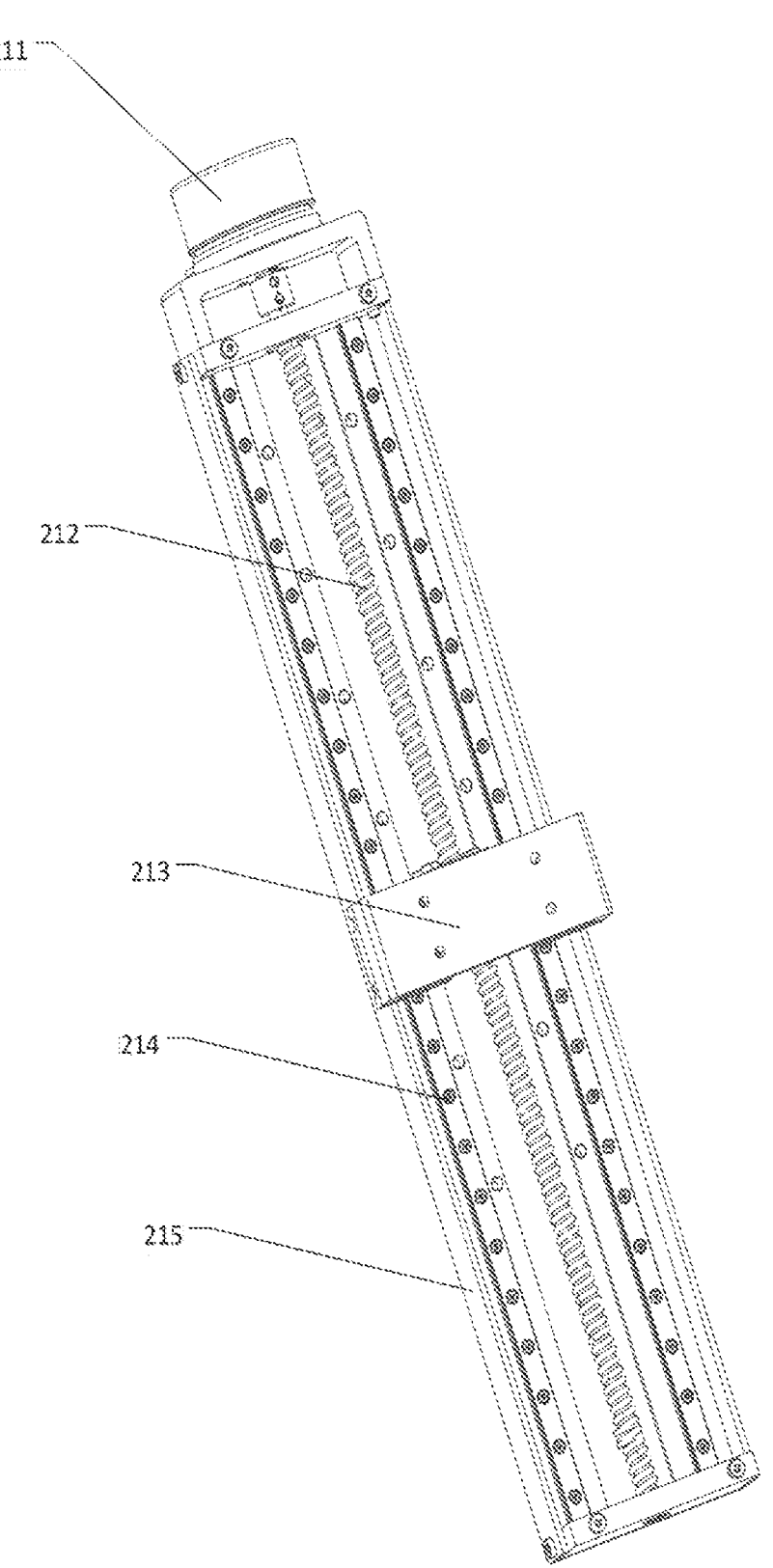
FIG. 14 is the schematic diagram of the translational probe unit of an endoscopic surgery platform of the present invention.

Wherein: 1, surgical bed; 11. surgical table; 12, support frame; 13, base; 14. moving caster; 2. surgical manipulator; 21, translation probe unit; 211, translational probe motor; 212, screw; 213, surgical instrument mounting plate; 214, linear slide rail; 215, protective cover; 22, deflection unit; 221, deflection motor; 222, second transmission bevel gear; 223, the first transmission bevel gear; 224, arc slide rail; 225, arc mounting plate; 226, drive wheel; 227, guide wheel; 228, driven wheel; 23, axial rotation unit; 24, rotary storage mechanism; 25, lifting mechanism; 251, lifting connection plate; 252, transmission gear; 253, worm gear motor; 254, vertical rack; 255, lifting column; 256, T-shaped connecting column; 3. positioning mechanism; 31, lateral moving pair; 311, positioning iron bar; 312, lateral slide rail; 313, lateral moving platform; 314, electromagnet; 32, longitudinal moving pair; 321, longitudinal moving platform; 322, longitudinal slide rail; 323, guide rail clamp; 33, long magnetic grating ruler; 34, reading head; 35, short magnetic grating ruler.

DETAILED DESCRIPTION OF THE EMBODIMENTS

The following section will provide a more comprehensive description of the invention, incorporating the accompanying illustrations. It is important to note that this embodiment is presented as an example and is not intended to restrict the scope of the invention. Rather, this embodiment offers a detailed method for implementing the technical scheme outlined herein, including specific steps for carrying out the invention.

An endoscopic surgical platform has been developed, consisting of a surgical bed 1 and several surgical manipulators 2. The manipulators 2 are arranged in a matrix pattern on either side of the surgical bed 1, and a positioning mechanism 3 is located at the base of the bed. This mechanism enables the surgical manipulators 2 to be stored at the bottom of the surgical bed 1.

The surgical manipulators 2 are arranged in a rectangular grid on both sides of the surgical bed 1. Each manipulator is capable of independent movement, allowing for flexible preoperative positioning without interfering with other manipulators. The embodiment described here includes four surgical manipulators arranged in pairs on either side of the surgical bed 1. Each surgical manipulator 2 is equipped with a telecentric mechanism at the top, which enables precise, fixed-point motion around the surface incision. This mechanism is used to adjust the position and posture of the two types of end-effectors on the surgical instrument or endoscope so that they can reach the internal operation area and perform the necessary procedure.

The positioning mechanism 3 includes a plurality of lateral moving pairs 31 corresponding to the position of multiple surgical manipulators set at the bottom of the surgical bed 1 and used to move along the length direction of the surgical bed 1, and a plurality of longitudinal moving pairs 32 corresponding to the position of multiple surgical manipulators set at the bottom of the operating bed 1 and used to move along the width direction of the surgical bed 1. The longitudinal moving pair 32, the lateral moving pair 31 and the surgical manipulator are connected one by one in turn, which is mainly used to adjust the position of the end of the manipulator before the operation, so that the far center point is aligned with the set surgical incision.

Preferably, the surgical bed 1 would consist of a surgical table 11, a support frame 12, a base 13, and a moving caster 14 arranged in sequence from top to bottom. The surgical table 11 is constructed from aluminum alloy plates and used to provide a surgical operation platform and accommodate patients. The support frame 12 is made of strong, heavy-duty profiles and utilized to support the panel of the operation bed 1, four surgical manipulators, and the patients. Two angular codes and profile screw holes are used to connect the top of the support frame 12 to the surface of the surgical bed 1. The support frame 12 is secured to the surgical bed 1 and the base 13 by eight angular codes below.

The lateral moving component 31 consists of a lateral slide rail 312 that is fixed to the bottom of the surgical table 11, a positioning iron bar 311 that is parallel to the slide rail, and a lateral moving platform 313. One side of the platform 313 is connected to the slide rail 312 through a slider, and the opposite side is magnetically adsorbed and positioned by the electromagnet 314 and the positioning iron bar 311. The electromagnet 314 generates an electromagnetic force that holds the lateral moving platform 313 in place, preventing it from moving along the lateral slide rail 312, thereby facilitating precise positioning.

Preferably, the longitudinal moving pair 32 comprises a longitudinal slide rail 322 that is fixed on the opposite side of the lateral moving platform 313, a longitudinal moving platform 321 that is slidingly connected to the longitudinal slide rail 322 with a slider on one side, and a guide rail clamp 323 that is used to position the longitudinal moving platform 321 on the longitudinal slide rail 322. The other side of the longitudinal moving platform 321 is linked to the surgical manipulator. After the surgical manipulator is positioned along the width direction of the surgical bed 1, the grip on the guide rail clamp 323 is tightened. The brake element on the guide rail clamp 323 tightly clamps both sides of the longitudinal slider, thereby fixing the longitudinal moving platform 321 in place.

Preferably, a long magnetic grating ruler 33 and a short magnetic grid ruler are also fixed to the bottom end of the surgical table 11 and the position parallel to the lateral slide rail 312, and to the bottom of the longitudinal moving platform 321 and the position parallel to the longitudinal slide 322. The reading head 34 is installed on both the lateral moving platform 313 and the longitudinal moving platform 321, each of which is suitable for the long magnetic grating ruler 33 and the short magnetic grid ruler 35. In this implementation case, the long magnetic grating ruler 33 and the short magnetic grating ruler 35 are arranged directly above their corresponding reading head 34, and each is positioned close to its respective reading head 34. By energizing the reading head 34, the movement of the lateral moving platform 313 and the longitudinal moving platform

321 can be detected and recorded by the long magnetic grating ruler 33 and the short magnetic grid ruler 35, respectively.

Bedside baffles are installed at both ends of the bottom of surgical table 1 to prevent the lateral moving platform 313 from colliding with the lateral slide rail 312.

Preferably, the surgical manipulators 2 consist of several components, including a rotary storage mechanism 24, a lifting mechanism 25, an axial rotation unit 23, a deflection unit 22, and a translational probe unit 21, which are sequentially linked to the longitudinal moving platform 321.

The rotary storage mechanism 24 comprises a storage joint module linked through a vertical mounting column to a longitudinal moving platform 321. The output end of the storage joint module connects with one end of the horizontal connecting column. This configuration permits the surgical manipulator to switch from the working attitude (vertical) to the storage position (horizontal) and work together with the two horizontal translation joints of the positioning mechanism 3, thus accomplishing the process of storage.

Preferably, the lifting mechanism 25 is composed of the lifting column 255, which is linked to the distal end of the T-shaped connecting column 256 and the horizontal connecting column. The lifting shell is connected to the lifting column 255 through vertical sliding, and the driving components are responsible for driving the lifting shell to move along the lifting column 255. These driving components comprise a worm gear motor 253 fixed inside the lifting shell with the aid of the lifting connection plate 251, a transmission gear 252 connected to the output end of the worm gear motor 253, and a vertical rack 254 engaged with the transmission gear 252. The vertical rack 254 is secured to the inner wall of the lifting column 255, which also has a vertical guide slide rail attached to it. The vertical guide slider is fixed on the lifting connection plate 251 and in a corresponding position of the vertical guide slide rail, forming a sliding attachment. After the motor shaft of the worm gear motor 253 is rotated, the output shaft of the worm reducer links up with the transmission gear 252, which meshes with the rack. Through the action of the gear rack, the lifting shell can rise and fall. Furthermore, since the worm gear motor 253 uses a worm reducer with worm wheel and worm self-locking, the power can only be output by the motor end, which ensures that the lifting mechanism 25 will not spontaneously fall under the impact of heavy loads applied from above.

In this particular configuration, a baffle plate is mounted at both ends of the vertical guide slide rail. The photoelectric switch on the slider serves to limit the stroke of the linear motion in the upward and downward directions. This switch detects the starting point of the stroke generated by the lifting mechanism 25.

The varying characteristics of the human abdomen necessitate the use of different heights for surgical incisions based on the specific surgical procedure. In order to achieve this, the lifting mechanism 25 must be appropriately adjusted to regulate the height of the end of the preoperative surgical manipulator. This ensures that the telecentric point of the telecentric mechanism on the surgical manipulator 2 is consistent with the height of the surgical incision.

Preferably, the axial rotation unit 23 is composed of an axial rotary joint module that is securely fastened to the lifting shell. The axial rotary joint module is then connected to the deflection unit 22 at its output end.

Preferably, the deflection unit 22 is comprised of several components, including an arc mounting plate 225, an arc slide rail 224 fixed to one side of the mounting plate, multiple guide wheels 227 rotating on the other side of the arc mounting plate 225, and a drive wheel 226 and a driven wheel 228. The guide wheels 227, the drive wheel 226, and the driven wheel 228 are arranged in an arc shape with the same radian as the arc slide rail 224. The drive wheel 226 is concentrically connected to the first transmission bevel gear 223, which is in turn engaged with the second transmission bevel gear 222. The second transmission bevel gear 222 is connected to the output shaft of the deflection motor 221 fixed on the lateral shaft. The drive wheel 226, the multiple guiding wheels 227, and the driven wheel 228 are connected by wire rope transmission. The wire rope is connected to the translational probe unit 21 through an arc hole in the arc mounting plate 225, and the translational probe unit 21 is also connected to the arc slide rail 224. In this implementation case, the drive wheel 226, the driven wheel 228, and the guiding wheel 227 are all round wheels, each with grooves. Because the diameter of the round wheel with grooves is small, but the yaw motion angle is large, and the arc motion stroke is long, multi-ring winding wire rope is used on both the drive wheel 226 and the driven wheel 228, with the wire rope fixed in the step hole opened on the drive wheel 226 or the driven wheel 228 after multi-ring winding.

The transmission mechanism of the wire rope can be described as follows. Firstly, the deflection motor 221 drives the drive wheel 226 to rotate through the second bevel gear and the first bevel gear in a sequential manner. As the drive wheel 226 rotates, the wire rope wrapped around it is either relaxed or tightened. At the same time, the wire rope cooperates with the driven wheel 228 at the other end (for instance, if the wire rope on the drive wheel 226 is being continuously released, then the wire rope on the driven wheel 228 is simultaneously being continuously wound, and vice versa). This cooperation allows the wire rope to move along the arc of the guide wheel 227 and consequently guide the translation probe unit 21 to move during its motion. In this way, the transmission mechanism completes the closed-loop transmission and utilizes the wire rope to drag the load and transfer movement. The wire rope's small quality can effectively reduce the overall weight of the telecentric mechanism and contribute to the optimal design of the mechanism layout.

Preferably, the translation probe unit 21 includes a translation probe motor 211, a screw 212 and a ball nut which are connected in turn. The ball nut is connected to the surgical instrument mounting plate 213. The surgical instrument mounting plate 213 is equipped with surgical instruments. The surgical instruments are surgical instruments or endoscopes, and the operative parts of the surgical instruments or endoscopes enter the chest/abdominal cavity through the puncture channel at the surgical incision. The principle of linear motion is: in the transmission mechanism composed of ball nuts and screws, driven by the translational probe motor 211, the screw 212 rotates around its own axis, and the ball nut rotation is locked, so that the ball nut can only move linearly along the axis of the screw 212. Therefore, the surgical instrument mounting plate 213 is driven to move linearly along the linear slide rail 214, so as to drive the surgical instrument mounted on the surgical instrument mounting plate 213 to move along the axis of its operating rod.

Both sides of the surgical instrument mounting plate 213 slide along the linear slide rail 214 via a slider. The linear slide rail 214 on each side is firmly connected to the internal sides of the protective cover 215. The midpoint of the protective cover 215 is rotationally connected to the two ends of the screw 212. The external side of the protective cover 215 slides along the arc slide rail 224 via a slider, and it also slides along the arc mounting plate 225 through a wedge. One end of the double-head screw is firmly connected to the wedge, and the other end of the double-head screw is firmly connected to the wire rope after passing through the arc hole.

The working process begins by changing the surgical manipulator from the storage state to the working state, followed by adjusting the lifting mechanism 25, lateral moving pair 31, and longitudinal moving pair 32 to align the surgical instrument at the end of the surgical manipulator with the wound position based on the patient's chest and abdomen position and height on the surgical table 11. The worm gear motor 253 is then closed, and the longitudinal moving pair 32 and the lateral moving pair 31 are locked using electromagnet 314 and guide rail clamp 323, respectively. The axial rotation unit 23, deflection unit 22, and translation probe unit 21 can be controlled according to the operation's needs to execute the corresponding actions.

The storage process is as follows: firstly, the surgical instruments held on the surgical manipulator 2 are unloaded, and the locking state of the lateral moving platform 313 and the longitudinal moving platform 321 is released at the same time. Then, the surgical manipulator 2 is pushed horizontally, so that the surgical manipulator 2 is driven by the lateral moving platform 313 to approach the head of the surgical bed 1 along the lateral slide rail 312, and then the rotation of the rotary storage module is controlled to make the surgical manipulator 2 rotate from the vertical state to the horizontal state. Finally, the surgical manipulator 2 is pushed inward (that is, the surgical manipulator 2 is pushed to the center, and the surgical manipulator 2 can be first pushed horizontally, so that the surgical manipulator 2 moves inward under the action of the lateral moving platform 313, and then the surgical manipulator 2 is pushed longitudinally) to complete the storage operation. The reverse operation can transform the surgical manipulator 2 from the storage state to the working state.

Thus, the present invention employs a novel endoscopic surgical platform that can be integrated with the aforementioned surgical manipulator. This integrated form facilitates quick and easy accommodation of each surgical manipulator and is well-suited for multi-scene surgery mode.

Finally, it should be noted that the aforementioned embodiments are presented solely for the purpose of explaining the technical scheme of the invention and not to limit it in any way. Although the invention is described in detail with reference to the preferred embodiment, those skilled in the art should understand that the technical scheme of the invention can still be modified or replaced, and such modifications or equivalent substitutions will not fall outside the spirit and scope of the technical scheme of the present invention.

What is claimed is:

1. An endoscopic surgery platform, comprising a surgical bed and surgical manipulators, wherein the surgical manipulators are arranged on both sides of the surgical bed in a matrix arrangement, a positioning mechanism is arranged at a bottom of the surgical bed, and the surgical manipulators are stored at the bottom of the surgical bed through the positioning mechanism, the positioning mechanism comprises:

the surgical manipulators positioned on the bottom of the surgical bed, lateral moving pairs for moving along a length direction of the surgical bed, and longitudinal moving pairs connected to an output end of the lateral moving pairs respectively and used to move along a width direction of the surgical bed, wherein the longitudinal moving pairs, the lateral moving pairs and the surgical manipulators are connected one by one;

and wherein the surgical bed comprises a surgical table, a support frame, a base and a moving caster arranged from top to bottom, each of the lateral moving pairs comprises:

a lateral sliding rail fixed at a bottom of the surgical table, a positioning iron bar arranged in parallel with the lateral sliding rail, and a lateral moving platform, wherein a first side of the lateral moving platform is slidingly connected to the lateral sliding rail through a first slider, and the first side of the lateral moving platform facing the lateral sliding rail is also connected to the positioning iron bar by an electromagnet.

2. The endoscopic surgery platform according to claim 1, wherein each of the longitudinal moving pairs comprises a longitudinal slide fixed on a second side of the lateral moving platform, a longitudinal moving platform slidingly connected to the longitudinal slide on a first side through a second slider, and a guide rail clamp for positioning the longitudinal moving platform to the longitudinal slide, wherein a second side of the longitudinal moving platform is connected to each of the surgical manipulators.

3. The endoscopic surgery platform according to claim 2, wherein the bottom of the surgical table and a position parallel to the lateral sliding rail are also fixed with a long magnetic grating ruler; a bottom of the lateral moving platform and a position parallel to the longitudinal slide are also fixed with a short magnetic grating ruler; and reading heads suitable for the long magnetic grating ruler and the short magnetic grating ruler are set respectively on the lateral moving platform and the longitudinal moving platform.

4. The endoscopic surgery platform according to claim 2, wherein each of the surgical manipulator comprises a rotary storage mechanism, a lifting mechanism and a telecentric mechanism, wherein the rotary storage mechanism, the lifting mechanism and the telecentric mechanism are connected to a longitudinal moving platform in turn; the telecentric mechanism is a composite structure comprising an axial rotation unit, a deflection unit and a translational probe unit.

5. The endoscopic surgery platform according to claim 4, wherein the rotary storage mechanism comprises a storage joint module connected by a vertical mounting column and a longitudinal moving platform; and an output end of the storage joint module is connected to one end of a horizontal connecting column.

6. The endoscopic surgery platform according to claim 5, wherein the lifting mechanism comprises a lifting column connected to an other end of a T-shaped connecting column and the horizontal connecting column, a lifting shell slidingly connected to a vertical direction of the lifting column, and a driving component for driving the lifting shell to slide along the lifting column;

the driving component comprises; a worm gear motor fixed in the lifting shell by a lifting connecting plate, a transmission gear connected to an output end of the worm gear motor, and a vertical rack meshing with the transmission gear; the vertical rack is fixed on an inner wall of the lifting column; and the inner wall of the lifting column is also fixed with a vertical guide slide rail, which is fixed on a lifting connection plate and a position corresponding to the vertical guide slide rail; and a vertical guide slider is slidingly connected to the vertical guide slide rail.

7. The endoscopic surgery platform according to claim 6, wherein the axial rotation unit of the telecentric mechanism comprises an axial rotation joint module fixedly connected to the lifting shell; and an output end of the axial rotation joint module is connected to the deflection unit through a lateral rotation shaft.

8. The endoscopic surgery platform according to claim 7, wherein the deflection unit of the telecentric mechanism comprises; an arc installation plate, an arc slide rail fixed on a first side of the arc installation plate, guide wheels rotating on a second side of the arc installation plate, a drive wheel and a driven wheel;

wherein the guide wheels, the drive wheel and the driven wheel are enclosed in an arc shape with a same radian as the arc slide rail;

the drive wheel is concentrically connected to a first transmission bevel gear, the first transmission bevel gear is engaged with a second transmission bevel gear, and the second transmission bevel gear is connected to an output shaft of a deflection motor fixed on the lateral rotation shaft; and the drive wheel, the guiding wheels and the driven wheel are connected by wire rope transmission, and a wire rope is connected to a translational penetration unit through an arc hole opened on the arc installation plate, and the translational penetration unit is also connected to the arc slide rail.

9. The endoscopic surgery platform according to claim 7, wherein the translational penetration unit of the telecentric mechanism comprises a translational probe motor, a screw and a ball nut connected in turn, and the ball nut is connected to a surgical instrument mounting plate, and a surgical instrument is installed on the surgical instrument mounting plate; and both sides of the surgical instrument mounting plate are connected by a first sliding block and linear slide rails, and the linear slide rails on both sides are fixedly connected to both sides of an inner side of a protective cover, a middle of the protective cover is rotatably connected to both ends of the screw, an outer side of the protective cover is connected by a second sliding block and an arc slide rail, the outer side of the protective cover is also connected by a wedge block and an arc mounting plate, the wedge block is fixedly connected to a first end of a double head screw, and a second end of the double head screw is fixedly connected to the wire rope after passing through the arc hole.

* * * * *